United States Patent
Chiodo

(10) Patent No.: US 7,414,403 B2
(45) Date of Patent: Aug. 19, 2008

(54) IMAGING MACHINE / MRI POSITIONING ASSEMBLY FOR MAGNET COILS AND SPECIMENS AT THE SWEET SPOT OF AN IMAGING FIELD

(76) Inventor: Chris D. Chiodo, 29277 Newport, Warren, MI (US) 48093

( * ) Notice: Subject to any disclaimer, the term of this patent is extended or adjusted under 35 U.S.C. 154(b) by 538 days.

(21) Appl. No.: 10/631,226

(22) Filed: Jul. 31, 2003

(65) Prior Publication Data

US 2005/0027190 A1    Feb. 3, 2005

(51) Int. Cl.
*G01V 3/00* (2006.01)
*A61B 5/055* (2006.01)

(52) U.S. Cl. .................. 324/321; 324/318; 600/410; 600/411; 600/415

(58) Field of Classification Search ......... 324/300–322; 600/410, 411, 415, 421, 422
See application file for complete search history.

(56) References Cited

U.S. PATENT DOCUMENTS

| | | | | |
|---|---|---|---|---|
| 3,710,101 A | * | 1/1973 | O'Keeffe et al. ............. | 250/311 |
| 4,088,944 A | * | 5/1978 | Engler et al. ................ | 324/321 |
| 4,831,330 A | * | 5/1989 | Takahashi ................... | 324/318 |
| 4,926,125 A | * | 5/1990 | Roemer ....................... | 324/318 |
| 5,084,676 A | * | 1/1992 | Saho et al. .................. | 324/318 |
| 5,457,387 A | * | 10/1995 | Patrick et al. .............. | 324/318 |
| 5,550,472 A | * | 8/1996 | Richard et al. ............. | 324/320 |
| 5,590,655 A | * | 1/1997 | Hussman ..................... | 600/426 |
| 5,783,943 A | * | 7/1998 | Mastandrea et al. ......... | 324/318 |
| 6,208,141 B1 | * | 3/2001 | Amor et al. ................. | 324/318 |
| 6,411,187 B1 | * | 6/2002 | Rotem et al. ................ | 335/296 |
| 6,429,016 B1 | * | 8/2002 | McNeil ....................... | 436/47 |
| 6,657,433 B1 | * | 12/2003 | Locatelli et al. ............. | 324/318 |
| 6,686,740 B2 | * | 2/2004 | Tschirky et al. ............. | 324/321 |
| 6,741,079 B2 | * | 5/2004 | Hofmann et al. ............ | 324/321 |
| 6,833,704 B1 | * | 12/2004 | Murphy et al. .............. | 324/318 |
| 6,969,993 B2 | * | 11/2005 | Tschirky et al. ............. | 324/321 |
| 2002/0146347 A1 | * | 10/2002 | McNeil ....................... | 422/63 |
| 2005/0027190 A1 | * | 2/2005 | Chiodo ........................ | 600/415 |

* cited by examiner

*Primary Examiner*—Brij Shrivastav
*Assistant Examiner*—Tiffany A Fetzner
(74) *Attorney, Agent, or Firm*—Lawrence J. Shurupoff

(57) ABSTRACT

A system is provided for facilitating the imaging of a specimen, such as a laboratory rat, within an imaging machine such as an MRI machine. A sliding, self-centering interconnection is provided between a magnetic positioning and spacing assembly and a specimen positioning and retention assembly. Support and abutment surfaces are provided for facilitating the proper mounting locations of a gradient coil and probe coil within the main magnet coil and for optimally locating a specimen with respect to the main magnet coil and with respect to the gradient and probe coils.

21 Claims, 8 Drawing Sheets

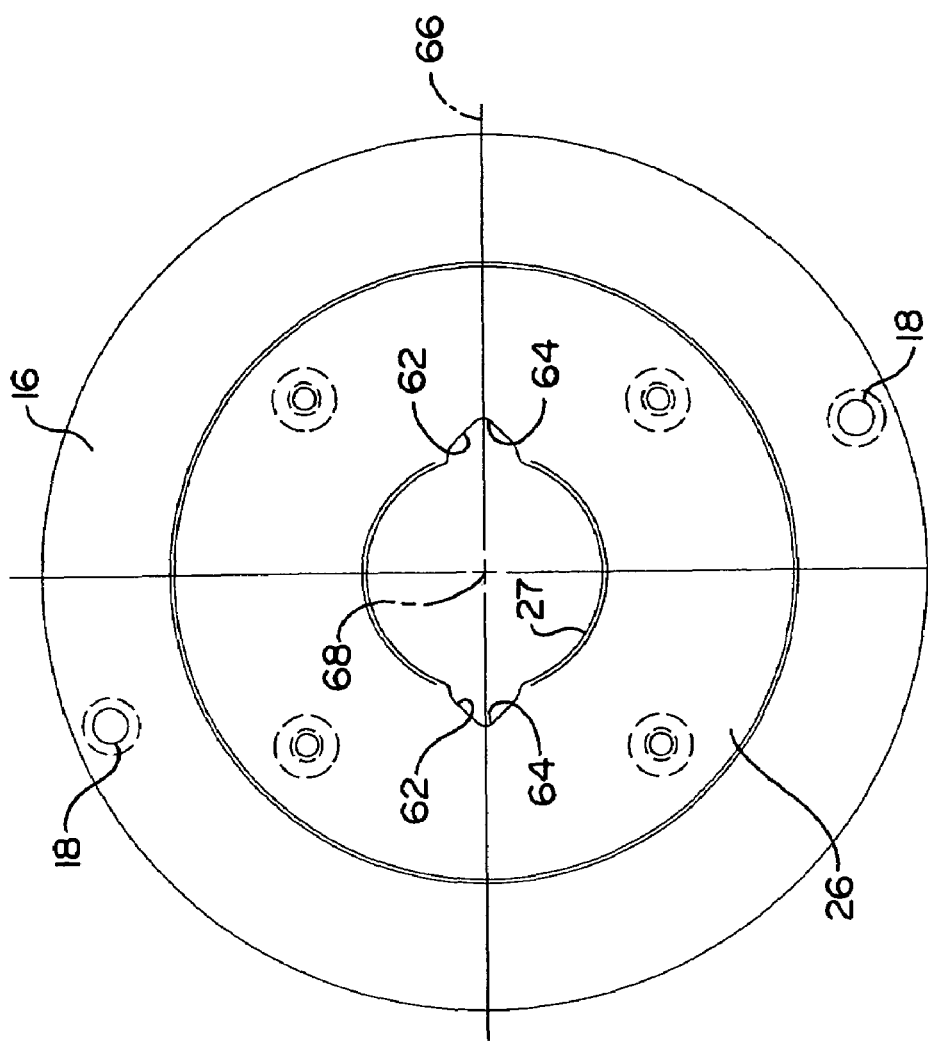
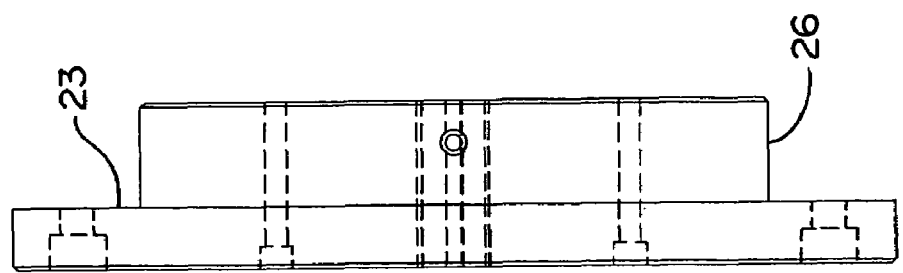

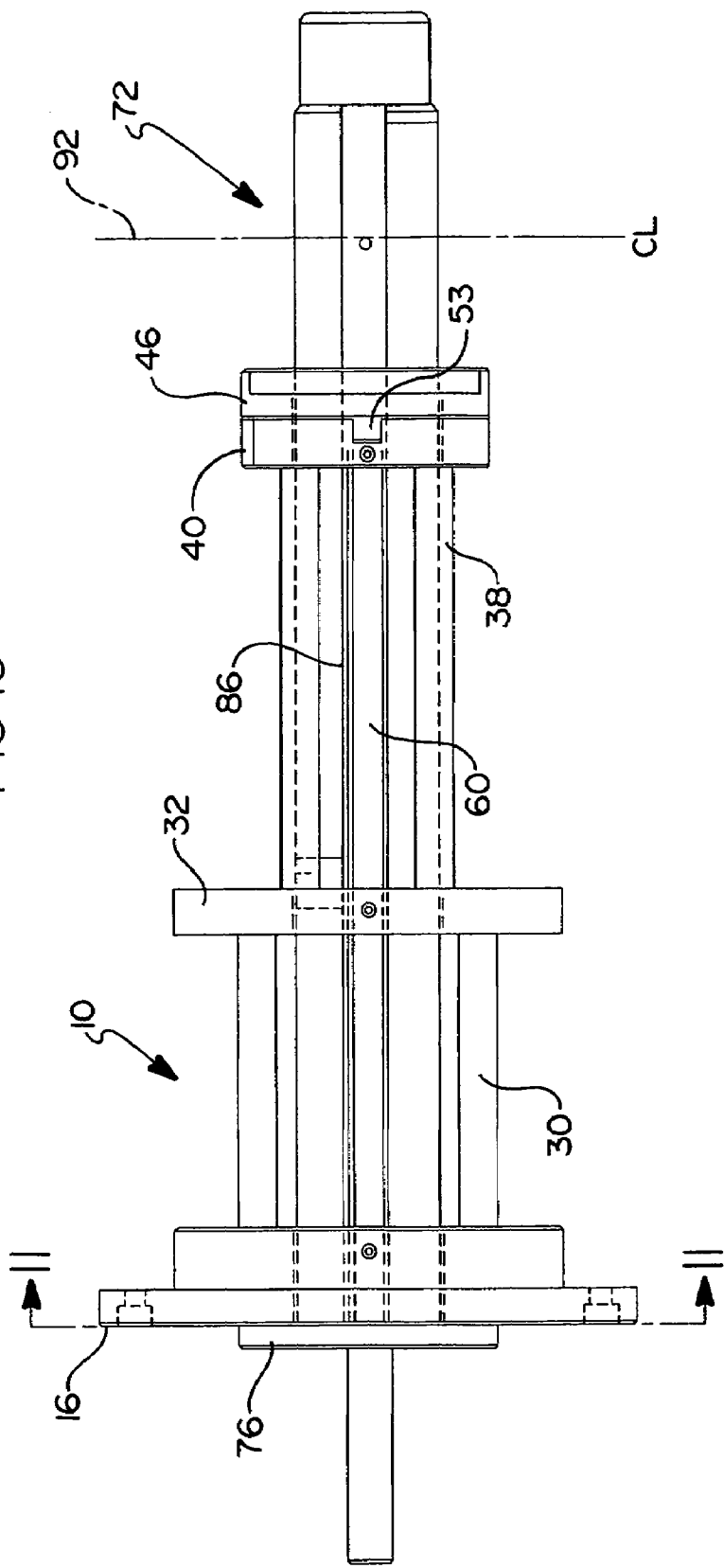

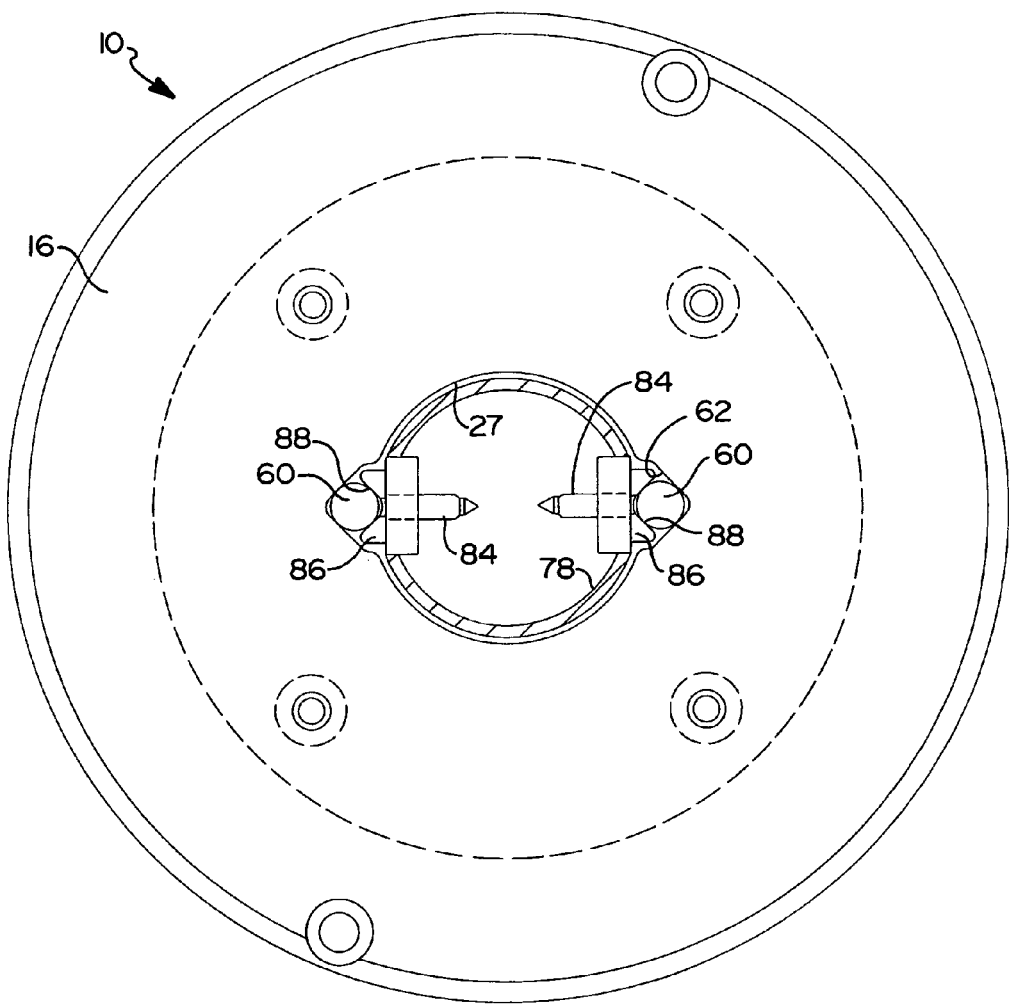
FIG II

IMAGING MACHINE / MRI POSITIONING ASSEMBLY FOR MAGNET COILS AND SPECIMENS AT THE SWEET SPOT OF AN IMAGING FIELD

BACKGROUND OF THE INVENTION

1. Field of the Invention

The present invention relates in general to an apparatus which spaces, locates and aligns one or more magnet coils concentrically within the bore of a main magnet coil of an MRI machine. The invention more particularly relates to such an apparatus which further concentrically positions a specimen tube accurately within the MRI bore along predetermined axial and radial planes for optimum imaging of the specimen.

2. Description of Prior Developments

In some magnetic resonance imaging (MRI) machines, a removable gradient coil is axially movably mounted with the bore of the main magnet coil with a simple sliding friction fit. This adjustable and removable fit allows an operator to selectively replace or interchange various gradient coils within the bore of the main coil to optimize the MRI machine for selected imaging applications.

While this feature has proved useful, it requires considerable time, effort and expertise to accurately reposition and install one replacement gradient coil in place of another. Prior replaceable gradient coils required trial and error adjustment of the axial position of the gradient coil within the main magnet coil bore, making repeatable imaging results difficult to achieve.

Even further adjustment of prior MRI machines was needed to accurately axially and cumferentially position and hold a specimen within the main magnet coil bore to achieve optimum imaging of the specimen. This problem is particularly, difficult in the case of laboratory animal specimens being imaged in the MRI machine, as the area being imaged is quite small. For example, the area imaged to cover a rodent brain is quite small and requires accurate adjustment and positioning within the MRI fields.

In order to further shape, condition and focus the magnetic field within the main coil bore, an additional coil, referred to as a probe coil, surface coil or radio frequency coil can be provided within the main coil bore. This coil must be carefully aligned axially, radially and circumferentially (clockwise) within the main coil bore and further carefully positioned with respect to the gradient coil and with respect to the specimen being imaged. Alignment of this probe coil has required considerable time, effort and expertise.

In some cases, it is desirable to interchange various probe coils to adapt the MRI machine for specific applications. It can be appreciated that such replacement can involve considerable time, effort and expertise in order to achieve optimum alignment with the other magnet coils and with the imaging area of the specimen.

In each of the cases noted above, the respective coil and specimen positioning and locating procedures must not only be accurate, but also highly repeatable so that results may be accurately duplicated for verification, sampling and proofs. Because of the trial and error positioning of magnets and specimens associated with prior procedures, accurate repeatable imaging results have been difficult to achieve.

SUMMARY OF THE INVENTION

The present invention has been developed to meet the needs noted above with a relatively easy to use coil and specimen holder assembly. The present invention provides a positioning and spacing assembly for quickly and easily locating a gradient coil within the bore of an MRI main magnet. The assembly also provides for the easy replacement of the gradient coil as well as for the accurate spacing and positioning of a probe coil with respect to the main coil, gradient coil and specimen imaging area.

The present invention further provides for the easy and accurate placement of a specimen holder within the bore of the main magnet coil. The specimen holder is not only positioned accurately and concentrically along the axial length of the bore of the main magnet coil, but also along a predetermined plane extending through the axis of the main magnet coil. This alignment is achieved with a tongue-in-grove or rail-in-groove sliding interconnection between the specimen holder and the positioning and spacing assembly.

Through use of the present invention, a specimen, such as a live rodent, may be accurately held in position within a specimen holder through the use of a pair of ear bars or other holding apparatus. The ear bars can be located in a horizontal or, other plane at or adjacent to the axial center or midpoint of the main magnet coil bore, and advantageously along the axis of the main magnet coil bar at the optimum location for imaging.

The present invention further provides accurate, highly repeatable positioning, spacing and concentric mutual alignment among a gradient coil, probe coil and specimen holder, all mutually aligned within the bore of a main magnet coil of an MRI machine for producing optimum imaging results. The invention may also be used in other imaging apparatus such as CAT scan, PET scan, and X-ray apparatus for accurately positioning a specimen within such apparatus. In such cases, magnets may or may not be positioned by the invention.

The aforementioned objects, features and advantages of the invention will, in part, be pointed out with particularity, and will, in part, become obvious from the following more detailed description of the invention, taken in conjunction with the accompanying drawing, which form an integral part thereof.

BRIEF DESCRIPTION OF THE DRAWINGS

In the drawings:

FIG. 5 is rear view of the front mounting plate of FIG. 1;

FIG. 6 is a side view of FIG. 5;

FIG. 10 is a side view of the specimen positioning assembly of FIG. 7 inserted within the positioning assembly of FIG. 3; and FIG. 11 is a front sectional view of FIG. 10, taken along line 11-11 thereof.

In the various view of the drawings, like reference characters designate like or similar parts.

DETAILED DESCRIPTION OF THE PREFERRED EMBODIMENT

Figure 1:
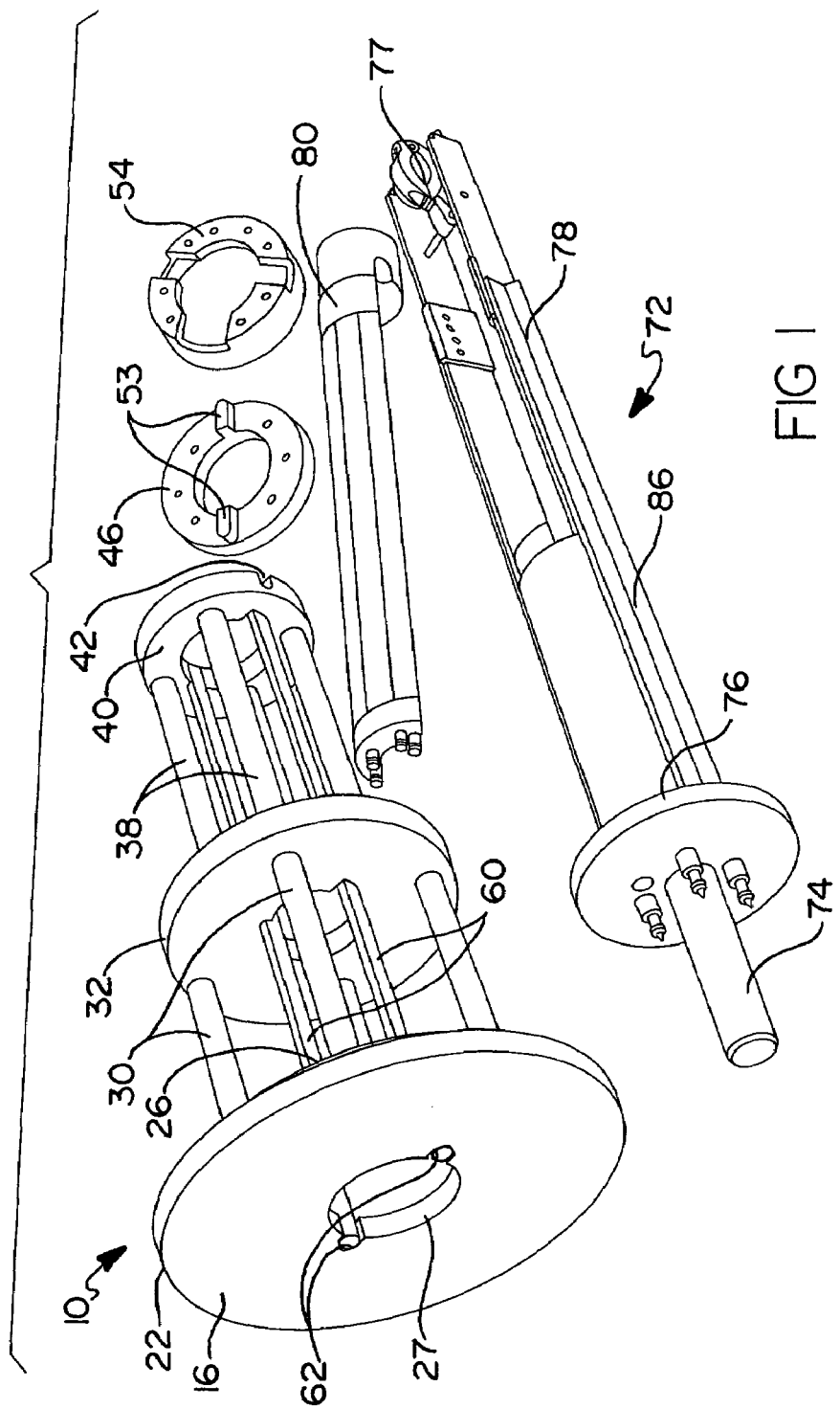
FIG. 1 is a front right top perspective view of a representative embodiment of a positioning assembly constructed in accordance with the present invention and showing the specimen positioning assembly removed for clarity.
Figure 2:
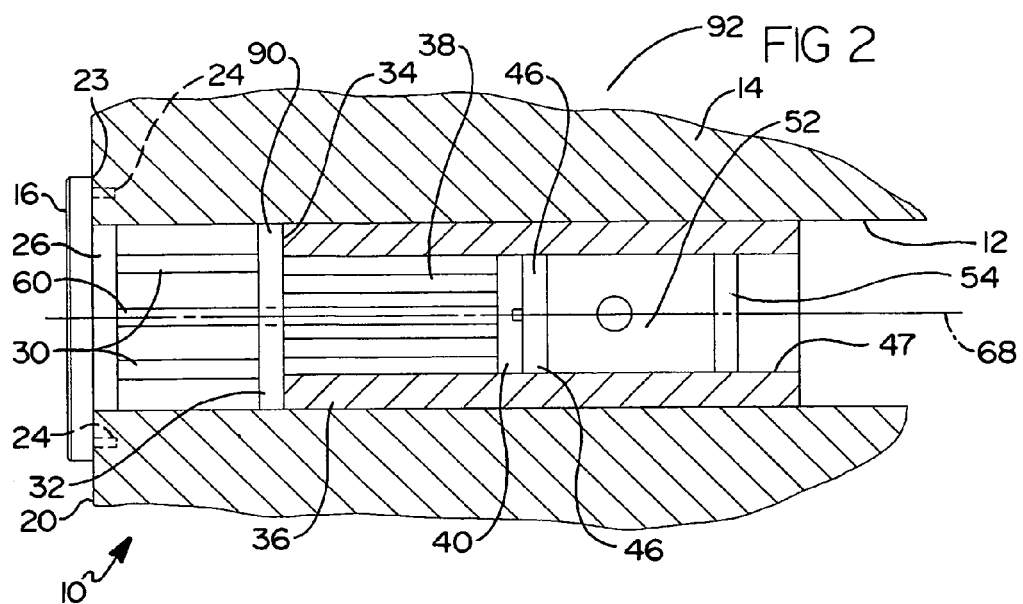
FIG. 2 is schematic side view, partly in axial section, of a positioning assembly constructed in accordance with the invention and mounted within the bore of a main magnet coil of an MRI machine.

The present invention will now be described in conjunction with the drawings, beginning with FIGS. 1, 2 and 3, which show a positioning assembly 10 adapted for use within the magnet coil bore 12 (FIG. 2) of a main magnet 14 of an MRI machine or other apparatus. The positioning assembly 10 includes an annular front mounting plate 16, shown in detail in FIGS. 4, 5 and 6, which axially, radially and circumferentially locates the assembly 10 with respect to the main magnet 14. As seen in FIGS. 4 and 5, the front mounting plate 16 includes a pair of through bores 18 for keying and aligning and mounting the assembly 10 to a pair of matching threaded bores on the front face 20 of the main magnet 14. Screws, bolts or other fasteners may be used to mount the assembly 10 to the main magnet, 14 via mounting plate or mounting member 16. Of course, other keying and alignment means may be used other than complimentary fastening bores on the assembly 10 and magnet 14.

Mounting plate 16 includes an outer or front flange 22 having an inner face 23 which is securely bolted via the through bores 18, or otherwise secured or clamped to the front face 20 of the main magnet coil 14. Matching bores 24 (FIG. 2) in the front face 20 of the magnet coil 14 align with the through bores 18 to accurately position the assembly 10 axially, radially and circumferentially (or clockwise) with respect to the bore 12 of the magnet coils of the main magnet 14.

The mounting plate 16 further includes an annular boss or plug portion 26 extending or projecting inwardly from inner face 23. Plug portion 26 is dimensioned to form a close sliding fit within the magnet coil bore 12 so as to coaxially center and support the assembly 10 within bore 12. A central aperture or bore 27 (FIG. 5) is formed through plate 16 and plug portion 26 to receive a specimen holder, as described below.

Four front spacer bars or rods 30 are rigidly and symmetrically mounted on their front ends to the plug portion 26 of the front mounting plate 16. The front spacer bars 30 are mounted on their opposite inner ends to an annular gradient coil locator plate 32.

The axial spacing between the inner face 23 of the front mounting plate 16 and the inner face 34 of the locator plate 32 is accurately dimensioned to control and set the axial placement of a gradient coil 36 (FIG. 2) and to properly position the gradient coil 36 with respect to a probe coil and specimen holding assembly, as described further below. The outer diameter of the gradient coil locator plate 32 is accurately dimensioned to closely and snugly fit within the main magnet coil bore 12 with a close sliding fit to provide further support and alignment for the positioning assembly 10.

Four rear or inner spacer bars or rods 38 are symmetrically mounted on their front ends to the inner face 34 of the gradient coil locator plate 32. An annular probe spacer plate 40 having a diameter less than that of plug 26 and locator plate 32, is rigidly mounted to the inner ends of the inner spacer bars 38. The diameter of the probe spacer plate is dimensional to fit closely within the bore, of a probe coil, as described below. A pair of diametrically opposed keying slots or recesses 42 is formed within the inner face 44 of the probe spacer plate 40 for receiving complementary keying projections on a probe coil cap, as discussed below.

The axial spacing of the inner or rear face 44 of the probe spacer plate 40 from the inner or rear face 23 of the front flange 22 is tightly controlled so as to provide an accurately axially-positioned radial mounting surface for receiving and abutting a probe coil front mounting ring or mounting cap 46. Front mounting cap 46 has a flat annular front face 48 (FIG. 3) which, when positioned in use, is tightly pressed against the inner face 44 of the probe spacer plate 40.

It should be noted that all of the previously identified components, except for the cap 46 which is not necessarily fixedly fastened to the assembly 10, may be securely fastened together with plastic fasteners such as Nylon plastic screws. That is, the front spacer bars 30 may be attached to the front mounting plate 16 and to the coil locator plate 32 with plastic screws. The inner spacer bars 38 may likewise be attached to the coil locator plate 32 and to the probe spacer plate 40 with plastic screws. All components of the positioning assembly 10, except for the magnet coils, can be advantageously formed of plastic materials such as Delrin plastic or Nylon plastic.

The front probe coil mounting cap 46 is formed with an annular recessed pocket 50 for snugly receiving the front end of a cylindrical probe coil 52 or similar magnet coil. The cap 46 may be securely and tightly retained on the probe coil 52 with plastic screws or other mounting means. The axial thickness of the mounting cap 46 is carefully dimensioned such that probe coil 52 will be optimally positioned within the bore 12 when the cap 46 and probe coil 52 are properly mounted to the probe spacer plate 40. This mounting is achieved by pressing and fully seating a pair of mounting and keying projections 53 provided on the front face of the front cap 46.

The substantially equal outer diameters of both the probe spacer plate 40 and the front probe coil mounting cap 46 are accurately dimensioned to fit within the inner bore 47 of the gradient coil 36 with a close sliding friction fit. This close fit aids in coaxially aligning the gradient coil 36 and probe coil 52 with the main magnet bore 12 and around the positioning assembly 10.

A probe coil inner-mounting cap 54 is provided with a pocket 56 for receiving the inner end of the probe coil 52 with a snug fit. Cap 54 may be attached to the probe coil 52 with nylon screws or similar fasteners. The probe coil inner mounting cap 54 is dimensioned with a diameter the same as that of the front probe coil mounting cap 46 for a snug fit within gradient coil bore 47. This provides further support and alignment of the gradient coil 36 and probe coil 52 within the magnet bore 12.

A pair of cylindrical rods 60 mounted at diametrically spaced positions on the radially inner surfaces of each of the front mounting plate 16, the gradient coil locator plate 32 and the probe spacer plate 40. Plastic screws 61 may be radially threaded through the outer radial surface of these annular components and into the cylindrical rods 60 50 as to hold the rods in axial and radial alignment with respect to each other and with respect to the positioning assembly 10.

Contoured notches or V-shaped grooves 62 may be formed at diametrically opposed locations in the walls of the inner bores of each of the front mounting plate 16, the gradient coil locator plate 32 and the probe spacer plate 40 to receive and firmly seat the cylindrical rods 60 to each respective component. As represented schematically in FIGS. 2 and 5, when the positioning assembly 10 is mounted within the main coil bore 12 and secured to the front face 20 of the magnet 14, the V-grooves 62 are located with their vertices 64 centered on a horizontal plane 66 which passes through the central axis 68 (FIG. 2) of the positioning assembly 10. As explained further below, the cylindrical rods 60 provide a self-centering pair of axially-extending support surfaces upon which a specimen positioning assembly is slidably mounted.

As seen in FIGS. 7, 8, 9 and 10, a specimen positioning assembly 72 includes a handle 74 mounted to a circular end plate 76: A specimen tube 78 is mounted to the end plate 76 and forms an internal chamber within which a laboratory specimen, such as a laboratory rat, may be secured for imaging within an MRI machine.

A semi cylindrical access door 80 is removably mounted on the inner end of specimen tube 78 to allow for insertion and removal of a specimen. Various specimen holders or specimen retention devices 77, may be mounted in the front end of the specimen tube 78. The abutment of the inner face of end plate 76 against the outer face of the front mounting plate 16 accurately determines the relative location of the specimen and specimen holder 77 with respect to the main magnet 14, gradient coil 36 and probe coil 36. That is, the axial length between the inner face 82 of the end plate 76 and the specimen imaging area within the tube is selected to axially locate and center a specimen within an optimum imaging location determined by the relative locations of the assembly 10, the main magnet 14, gradient coil 36 and probe coil 52.

In order to properly center the specimen positioning assembly 72 within the positioning assembly 10, a pair of side rails 86 is mounted on diametrically opposite sides of the specimen tube 78, as seen in FIGS. 8, 9, 10 and 11. All component parts of the specimen positioning assembly 72, including fasteners, are advantageously formed of plastic, such as Nylon plastic or Delrin plastic.

The location of the side rails 86 is referenced to the location of the specimen holder 77 such that a specimen is securely held at a fixed predetermined axial spacing from the inner face 82 of the end plate 76. Moreover, by aligning the specimen holder 77 with the side rails 86, the specimen will be held in a preferential horizontal plane.

For example, "ear bars" 84 (FIGS. 7 and 11) may be mounted on diametrically opposite sides of the specimen tube 78, and arranged radially perpendicular to the longitudinal axes of the side rails 86. When a rat or other specimen is clamped within the specimen tube 78, the ear bars 84 are adjusted radially inwardly to secure the specimen's head, via its ear openings, in a predetermined horizontal plane.

By rotatably adjusting the orientation of the ear bars 84 or other specimen holder 77, the specimen may be positioned in virtually any desired rotational position within the specimen tube 78.

Figure 9:
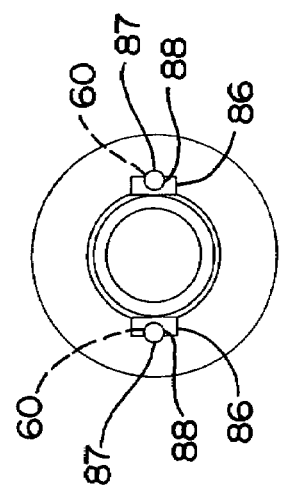
FIG. 9 is a rear view of FIG. 7.

As further seen in FIGS. 9 and 11, the side rails 86 are each formed with an outwardly facing longitudinally or axially-extending V-shaped groove 88, which is dimensioned to slidably and securely receive the cylindrical rods 60 on the positioning assembly 10. The cylindrical circular surfaces 87 on the rods 60 provide a self-centering effect or action on the specimen positioning assembly 72, as the circular outer sliding surfaces on rods 60 tend to center themselves with the V-shaped grooves 88 extending axially along the side rails 86. This adds significantly to the accurate alignment of the specimen position assembly 72 within the magnet bore 12.

In use, an operator inserts the positioning assembly 10 into the bore 12 of an MRI machine and fastens the front flange 22 to the front face 20 of the magnet coil 14. This axially, radially and circumferentially aligns the assembly 10 within the bore 12. The operator then inserts a gradient coil 36 into the opposite end of the magnet bore 12 and slides the gradient coil over the probe spacer plate 40, until the front end 90 (FIG. 2) of the gradient coil 36 firmly abuts the inner face 34 of the gradient coil locator plate 32. This aligns the gradient coil 36 in the proper axial position, concentrically and coaxially within the magnet bore 12.

Figure 3:
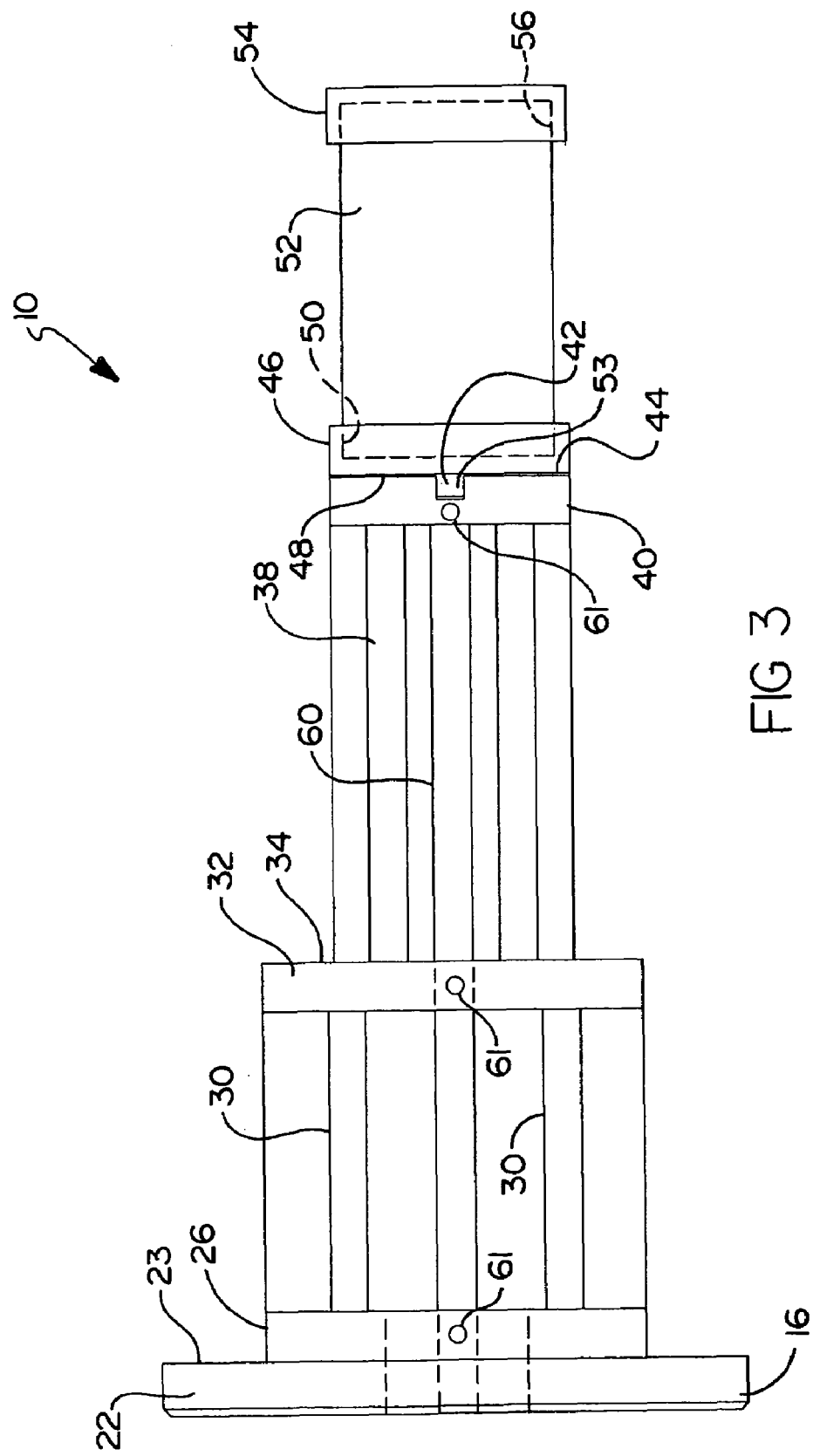
FIG. 3 is a side view of the positioning assembly of FIG. 1.
Figure 4:
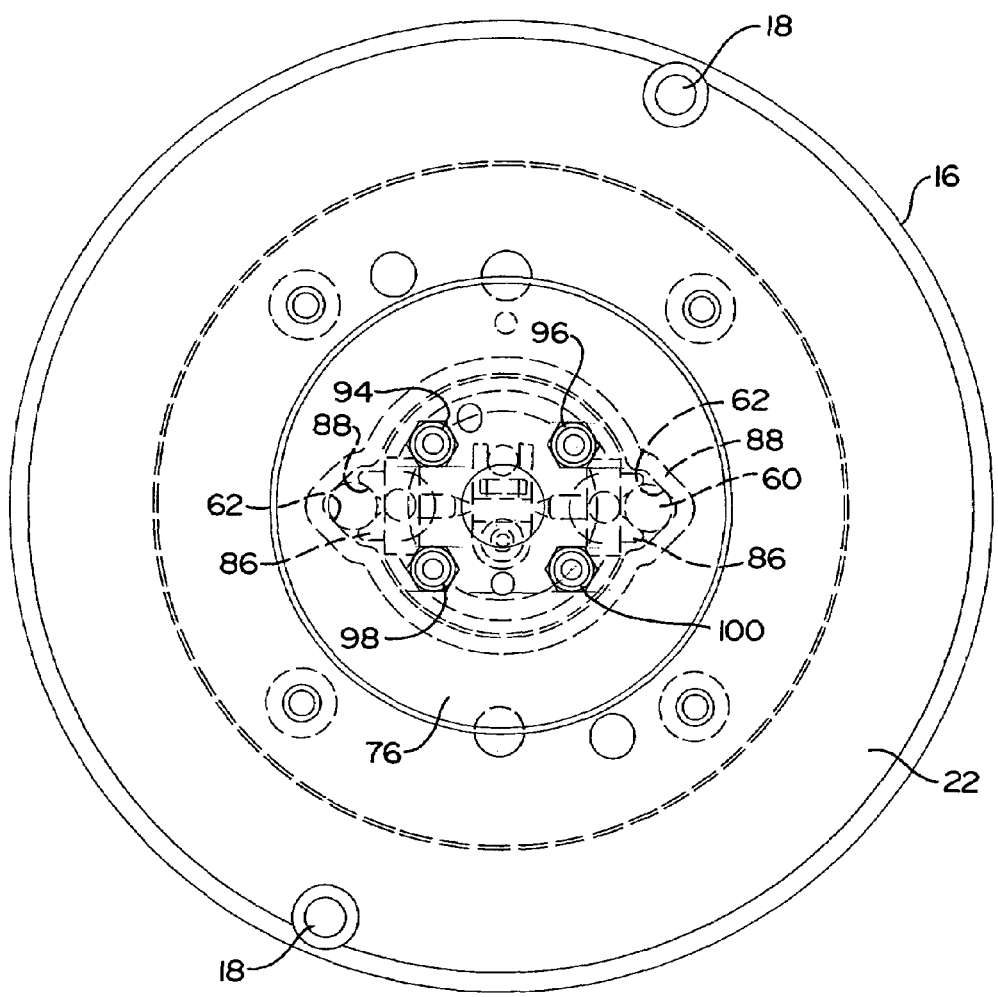
FIG. 4 is a front view of the positioning assembly of FIG. 3 with the specimen positioning assembly of FIG. 7 inserted therein.
Figure 7:
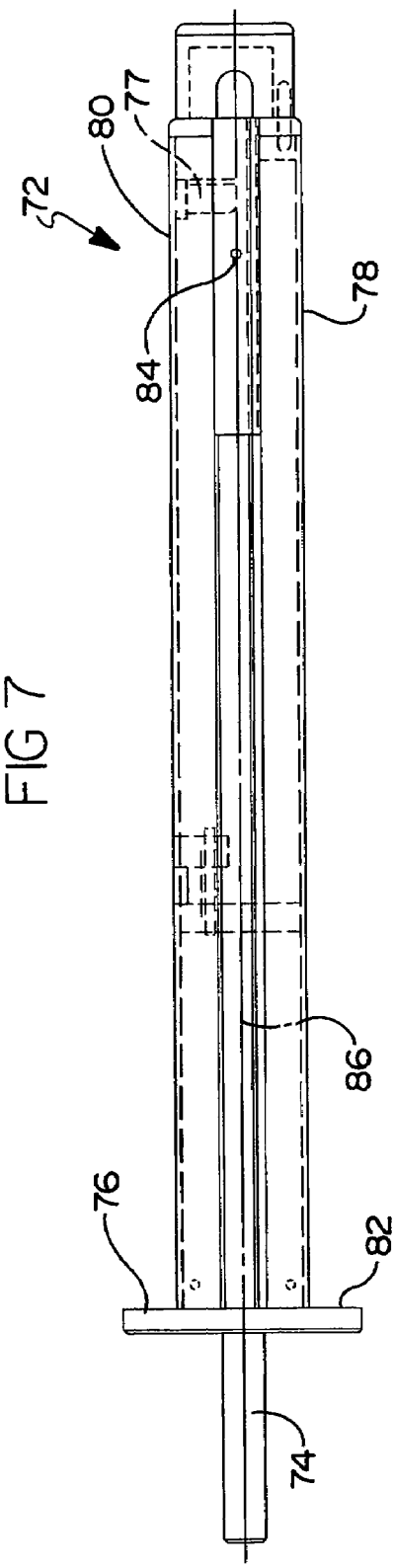
FIG. 7 is a side view of a specimen positioning assembly adapted for use with the positioning assembly of FIGS. 1 and 3.

The probe coil 52, with the front and inner mounting caps 46, 54 attached, is then axially inserted into the bore 47 (FIG. 2) of the gradient coil 36 and manipulated or rotated until the axially-extending keys 53 securely axially seat and nest within the matching recesses or keying slots 42 in the probe spacer plate 40 (FIG. 3). This accurately positions the probe coil 52 in a preferential axial, radial and circumferential position with respect to the position of the main magnet 14, gradient coil 36 and specimen positioning assembly 72 (and its specimen holder 77) when the specimen positioning assembly is subsequently mounted within the magnet bore 12.

Once the gradient coil 36 and probe coil 52 are fully seated on the positioning assembly 10, the specimen positioning assembly 72 is axially inserted into the central bore 27 in the front mounting plate 16. The V-grooves 88 in the side rails 86 of the specimen positioning assembly 72 are guided over the cylindrical rods 60 mounted in the positioning assembly 10.

The specimen positioning assembly 72 is pushed along the rods 60 and through the central bores in the plates 16, 32 and 40 until end plate 76 abuts the front mounting plate 16. This results in optimum placement of the specimen in the positioning assembly 10. For example, the axes of the ear bars 84 are advantageously aligned to pass near or through the center line 92 (FIG. 10) of the MRI machine so that the specimen is imaged in the "sweet spot" of the imaging field.

Figure 8:
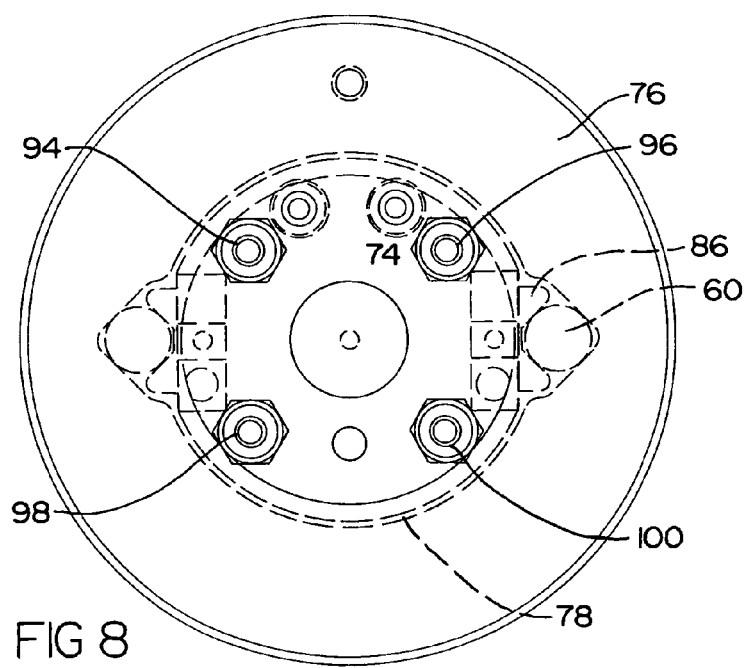
FIG. 8 is a front view of FIG. 7 and showing the relative sliding engagement between the rails and rods in dashed lines.

As seen in FIGS. 4 and 8; fluid or gas fittings 94, 96 maybe mounted in and through end plate 76 of the specimen positioning assembly 72 so as to allow for the respective delivery and exhaust of anesthetic gas or fluid into and out of the specimen tube 78. In a similar manner, fluid fittings 98, 100 may be mounted in and through end plate 76 so as to respectively allow for the circulation of cooling fluid, such as water, into and out of the specimen tube 78 for keeping the specimen cool.

There has been disclosed heretofore the best embodiment of the invention presently contemplated. However, it is to be understood that the various changes and modifications may be made thereto without departing from the spirit of the invention.

What is claimed is:

1. A specimen positioning system insertable within an axial bore of an imaging machine having an imaging field with a sweet spot, said system easily, accurately and repeatably positioning a non-human laboratory specimen in the sweet spot, said system comprising:
 a positioning assembly comprising;
  at least a first pair of support members insertable within the axial bore of the imaging machine;
  a first mounting member coupled to said first pair of support members and having a first abutment surface engageable with the imaging machine such that said positioning assembly is axially, radially and circumferentially positioned with respect to the axial bore of the imaging machine;
  a radially-extending second abutment surface provided on said positioning assembly; and
  said positioning assembly having an aperture receiving axial passage of the specimen into the axial bore of the imaging machine;
 a specimen positioning assembly comprising;
  at least a second pair of support members axially movable along said first pair of support members on said positioning assembly;

a retention device provided on said specimen positioning assembly and configured to pass through the aperture of said positioning assembly and secure the specimen in a fixed axial position;

a radially-extending third abutment surface provided on said specimen positioning assembly and engageable with said second abutment surface on said integrated positioning assembly; and an axially-extending interconnection provided between said first and second pairs of support members, said interconnection locating and supporting said specimen positioning assembly within the bore of the imaging machine and within the positioning assembly; and wherein axial insertion of said specimen positioning assembly through the aperture of said positioning assembly and along said axially-extending interconnection engages said radially-extending second and third abutment surfaces and thereby accurately and repeatably positions the specimen in the sweet spot of the imaging field so as to enable optimum repeatable imaging of the specimen.

2. The system of claim 1, wherein said first abutment surface comprises a radially-extending flange.

3. The system of claim 1, wherein said specimen positioning assembly further comprises a specimen chamber, and wherein said retention device is located in said specimen chamber.

4. The system of claim 1, wherein said positioning assembly further comprises a gradient coil locator plate axially spaced from said first abutment surface and configured to position a gradient coil within the axial bore of the imaging machine.

5. The system of claim 1, wherein said positioning assembly further comprises a probe coil spacer plate axially spaced from said first abutment surface and configured to position a probe coil within the axial bore of the imaging machine.

6. The system of claim 1, wherein said first, second and third abutment surfaces are located at predetermined axial positions upon abutment of said second and third abutment surfaces.

7. The system of claim 1, wherein said first and second abutment surfaces are located externally of said axial bore.

8. The system of claim 1, wherein said interconnection comprises a self-centering interconnection.

9. A specimen positioning system configured for use with an imaging machine having a sweet spot within an imaging field, comprising:

a positioning assembly mountable in a fixed position on said imaging machine;

a specimen positioning assembly removably, accurately and repeatably mountable in a predetermined position against said positioning assembly;

a specimen tube mounted on said specimen positioning assembly, said specimen tube having an internal chamber for holding a specimen;

a specimen retention device provided in said internal chamber and constructed in order to hold a specimen in a fixed position within said chamber;

a releasable self-centering interconnection provided between said positioning assembly and specimen positioning assembly, wherein movement of said specimen positioning assembly along said self-centering interconnection is axially limited at a predetermined axial position such that placement of the specimen positioning assembly into the positioning assembly along said self-centering interconnection up to said predetermined axial position locates the specimen within the sweet spot of the imaging field of the imaging machine.

10. The system of claim 9, further comprising a fluid fitting on said specimen positioning assembly and in fluid communication with said chamber.

11. The system of claim 9, wherein said specimen positioning assembly further comprises an access door allowing insertion and removal of the specimen into and out of said chamber.

12. The system of claim 9, wherein the specimen retention device comprises ear bars insertable into the specimen's ears.

13. The system of claim 9, wherein said interconnection comprises a sliding interconnection.

14. The system of claim 9, wherein said specimen positioning assembly further comprises an engagement member and wherein said movement of said specimen \ positioning assembly is axially limited by said engagement member.

15. The system of claim 14, wherein said positioning system further comprises an engagement surface engageable with said engagement member such that abutment is effected between said engagement member and said engagement surface at said predetermined axial position.

16. A coil and specimen positioning system easily positioning a non-human laboratory specimen in a predetermined position within a sweet spot of an imaging field in a bore of an MRI imaging machine and through a bore of a gradient coil located concentrically about the bore of the MRI imaging machine, said coil and specimen positioning system comprising:

an integrated coil positioning assembly comprising a first pair of support members insertable within the e bore of the MRI imaging machine and through the bore of the gradient coil, said coil positioning as assembly having an aperture axially receiving passage of said the specimen and having a first abutment surface engageable with the MRI imaging machine and a second abutment surface axially locating the specimen in the bore of the MRI imaging machine;

a specimen positioning assembly comprising a specimen retention device configured to fix the specimen in position and be insertable through the aperture of said integrated coil positioning assembly, and a second pair of support members insertable within said first pair of support members on said integrated coil positioning assembly, and a third abutment surface axially locating the specimen in the bore of the imaging machine;

an axially-extending interconnection provided between said first and second pairs of support members, said interconnection locating the specimen positioning assembly concentrically within the bore of the imaging machine and concentrically within the bore of the gradient coil; and wherein axial insertion of said specimen positioning assembly into said integrated coil positioning assembly abuts said second and third abutment surfaces and thereby positions the specimen accurately and repeatably in the sweet spot within the imaging field.

17. The system of claim 16, wherein said interconnection comprises a pair of rods and a pair of grooved rails.

18. The system of claim 16, wherein said interconnection comprises a self-centering interconnection.

19. The system of claim 16, further comprising a mounting member fixable to the MRI imaging machine, and wherein said first pair of support members is connected to said mounting member, and wherein said specimen positioning assembly is freely insertable into said mounting member and freely removable therefrom.

20. The system of claim 16, wherein said specimen positioning assembly comprises an end plate defining said third abutment surface and limiting insertion of said specimen positioning assembly into said MRI imaging machine.

21. A specimen positioning system configured for holding a laboratory specimen within a sweet spot of an imaging field within the bore of an imaging machine, comprising:

a positioning assembly fixed in position on the imaging machine, said positioning assembly comprising a boss portion dimensioned in order to form a close fit against and within the bore of the imaging machine in order to center and support the positioning system against and within the bore of the imaging machine;

a specimen positioning assembly removably mountable within the positioning assembly, said specimen positioning assembly comprising a specimen holder; and a self-centering interconnection provided between said positioning assembly and said specimen positioning assembly and comprising an abutment limiting axial movement of said specimen positioning assembly along said positioning assembly at a predetermined axial location such that a specimen held in said specimen holder is located within the imaging field sweet spot when movement of said specimen positioning assembly is limited at said predetermined axial location.

\* \* \* \* \*